United States Patent
Young, Sr. et al.

[11] Patent Number: 5,188,624
[45] Date of Patent: Feb. 23, 1993

[54] ABSORBENT ARTICLE WITH SUPERABSORBENT PARTICLE CONTAINING INSERT PAD AND LIQUID DISPERSION PAD

[75] Inventors: Richard H. Young, Sr., Puyallup; Michael R. Hansen, Everett; E. Peter Lancaster, Gig Harbor; Haresh R. Mehta, Federal Way; Christel Brunnenkant, Seattle, all of Wash.

[73] Assignee: Weyerhaeuser Company, Tacoma, Wash.

[21] Appl. No.: 467,797

[22] Filed: Jan. 16, 1990

[51] Int. Cl.$^5$ ............... A61F 13/15; A61F 13/20
[52] U.S. Cl. ............... 604/378; 604/358; 604/366; 604/368; 604/385.1
[58] Field of Search ............... 604/358, 366, 367, 368, 604/376, 378, 385.1

[56] References Cited

U.S. PATENT DOCUMENTS

| | | |
|---|---|---|
| 2,953,187 | 9/1960 | Francis, Jr. . |
| 3,777,758 | 12/1973 | Mesek et al. ............ 604/365 |
| 3,860,003 | 1/1975 | Buell . |
| 3,901,236 | 8/1975 | Assarsson et al. . |
| 4,009,313 | 2/1977 | Crawford et al. ............ 604/368 |
| 4,160,059 | 7/1979 | Samejima . |
| 4,187,342 | 2/1980 | Holst et al. . |
| 4,364,992 | 12/1982 | Ito et al. . |
| 4,392,908 | 7/1983 | Dehnel . |
| 4,397,644 | 8/1983 | Matthews et al. ............ 604/378 |
| 4,424,247 | 1/1984 | Erickson . |
| 4,492,729 | 1/1985 | Bannerman et al. . |
| 4,559,050 | 12/1985 | Iskra ............ 604/368 |
| 4,610,678 | 9/1986 | Weisman et al. . |
| 4,673,402 | 6/1987 | Weisman et al. ............ 604/378 |
| 4,676,784 | 6/1987 | Erdman et al. ............ 604/368 |
| 4,758,466 | 7/1988 | Dabi et al. . |
| 4,806,598 | 2/1989 | Morman . |
| 4,872,870 | 10/1989 | Jackson ............ 604/366 |
| 4,888,231 | 12/1989 | Angstadt ............ 604/376 |
| 4,935,022 | 6/1990 | Lash et al. ............ 604/368 |
| 4,988,344 | 1/1991 | Reising et al. ............ 604/368 |
| 5,002,814 | 3/1991 | Knack et al. ............ 604/365 |
| 5,057,166 | 10/1991 | Young, Sr. et al. ............ 156/62.2 |
| 5,064,689 | 11/1991 | Young, Sr. et al. ............ 427/202 |

FOREIGN PATENT DOCUMENTS 9111162 8/1991 World Int. Prop. O. ....... 604/385.1

OTHER PUBLICATIONS

TAPPI Standard Test Method T 489.

*Primary Examiner*—Randall L. Green
*Assistant Examiner*—P. Zuttarelli
*Attorney, Agent, or Firm*—Klarouist, Sparkman, Campbell, Leigh & Whinston

[57] ABSTRACT

A composite absorbent article is described having a plural layer absorbent core comprising a bonded insert pad and a dispersion pad. The insert pad preferably comprises binder coated fibers to which superabsorbent particles are adhered. By using heat fusible binders, a heat bonded superabsorbent containing insert pad is provided. The dispersion pad also typically comprises fibers and enhances the wicking of liquid throughout the insert pad. In addition, the insert pad may be bound to the dispersion pad at the interface between the pads to provide a stronger composite structure and to also entangle the fibers of the two pads at their interface to improve the wicking of liquid from the dispersion pad into the insert pad. In addition, hydrophilic fibers may be included in the insert pad to enhance the wicking of liquid into the insert pad. The use of surfactant materials in the binder enhances the vertical wicking characteristics of the composite pad. In addition, densification of the dispersion pad, within limits, also enhances the rewet characteristics of the article. In a disposable diaper construction, the insert pad is preferably positioned underneath the facing sheet of the diaper with the dispersion pad being positioned between the insert pad and the backing sheet of the diaper.

33 Claims, 4 Drawing Sheets

FIG. 1

FIG. 4 CORE (INSERT) DISPERSION LAYER (DL) DENSITY 0.05 g/cc

FIG. 5 CORE (INSERT) DISPERSION LAYER (DL) DENSITY 0.10 g/cc

ABSORBENT ARTICLE WITH SUPERABSORBENT PARTICLE CONTAINING INSERT PAD AND LIQUID DISPERSION PAD

The present invention relates to absorbent articles and more particularly to such articles which are disposable and which have an insert pad comprised of bonded fibers and superabsorbent particles and a liquid dispersion pad. The present invention particularly relates to disposable diapers having an insert pad positioned between a liquid permeable cover sheet and a liquid dispersion pad, the diaper also including a liquid impermeable backing sheet.

Disposable diapers are typically comprised of a liquid permeable facing sheet and a liquid impermeable backing sheet with an absorbent core positioned therebetween. It is common for the core to be made of wood pulp fibers or fluff. Although convenient, these early diapers were limited in their ability to absorb and retain volume of urine or other bodily fluid discharged into them during use, and therefore tended to leak.

To increase the capacity of absorbent products to absorb liquids, without unnecessarily increasing their bulk, highly liquid absorbing particles, frequently referred to as superabsorbent particles, have been incorporated into the core of diapers to increase their ability to absorb and retain liquids. In many cases, the superabsorbent particles have simply been mixed with the core forming fibers and included in the diaper structure. In this case, there is a tendency for the superabsorbent particles to migrate from the core. In addition, a phenomenon called gel blocking has been observed in some of these products. The term "gel blocking" describes a phenomenon that occurs when a hydrogel particle (or equivalently a fiber, etc.) is wetted. In such cases the particles at the surface of an article swell and inhibit liquid transmission to the interior of the article. Wetting of the interior subsequently takes place via a very slow diffusion process. This has meant that liquid absorption occurred at a much slower rate than the discharge of fluid to be absorbed. Consequently, the diaper or other absorbent structure may fail before the hydrogel material in the absorbent structure is fully wet.

Weissman, et al. U.S. Pat. No. 4,610,678 discusses a number of uses of superabsorbent particles in diaper structures. The Weissman, et al. patent describes a substantially unbonded structure wherein the number of fiber/fiber bonds, fiber/hydrogel particle bonds and hydrogel particle/hydrogel particle bonds is kept as low as reasonably possible. The structure has a weight ratio of fiber to hydrogel of from about 30/70 to about 98/2. The web structure of this patent is comprised of fibers and hydrogel and is densified or compressed to a density of from about 0.15 to about 1 gram per cubic centimeter. The moisture content of the structure is kept very low to ensure that the structure remains substantially unbonded. The insertion of these absorbent structures between an hourglass-shaped absorbent core typically found in a diaper and the liquid impermeable backing sheet of the diaper is also described in one example.

Another Weissman, et al. patent, U.S. Pat. No. 4,673,402, discloses a diaper with a dual-layered core. In a conventional manner, the diaper includes a liquid impermeable backing sheet, a liquid permeable top sheet, and an absorbent core positioned between the top sheet and backing sheet. The core has an upper fluid acquisition/distribution layer of a density of from about 0.05 to about 0.25 grams per cubic centimeter. The acquisition/distribution layer has from about zero percent to about eight percent hydrogel particles. In addition, the core includes a lower fluid storage layer, between the upper layer and the backing sheet, of a density of from about 0.06 to 0.3 grams per cubic centimeter, with about nine percent to about sixty percent by weight of hydrogel material. The lower layer occupies from about 0.25 to 1.0 times the area of the upper layer and is oriented such that at least about seventy-five percent of the hydrogel in the lower layer is found in the front two-thirds of the diaper structure.

Although these Weissman, et al. patents describe multilayer structures, a need exists for improved superabsorbent containing absorbent articles and for such articles with improved liquid absorbing characteristics.

SUMMARY OF THE INVENTION

In accordance with the present invention, a composite absorbent pad structure is comprised of a liquid dispersion pad of fibers which assists in dispersing liquid throughout the structure. In addition, the structure includes a substantially bonded insert pad. The insert pad includes fibers which are at least partially coated with a binder material, the fibers being bound together by the binder material to form the substantially bonded insert pad. In addition, these insert pad fibers have superabsorbent particles adhered thereto by the binder material. The superabsorbent particles are present in a range of from about ten percent to about eighty percent by weight of the insert pad.

Preferably the insert pad has a density of from about 0.05 grams per cubic centimeter to about 0.30 grams per cubic centimeter and most preferably the density ranges from about 0.18 grams per cubic centimeter to about 0.22 grams per cubic centimeter. In this latter range, and in particular at an optimum level of about 0.20 grams per cubic centimeter, the vertical wicking characteristics of the insert pad was enhanced.

When included in a disposable diaper or other absorbent article, the composite absorbent pad is preferably, although not necessarily, oriented such that the insert pad is positioned between a liquid permeable facing sheet of the article and the dispersion pad. A liquid impermeable backing sheet is also included with the dispersion pad being positioned between the insert pad and the backing sheet. With this construction, the rewet characteristic of the article is improved in comparison to the structure wherein the dispersion pad was positioned over the insert pad. In general, when a diaper is worn and a user discharges urine, urine will pass into the liquid dispersion pad and be carried or wicked by the liquid dispersion pad to previously dry areas of the insert pad to enhance the absorbance of the liquid into the insert pad.

In accordance with the present invention, the dispersion pad is compressed and densified to a limited extent. For example, the dispersion pad may be compressed to a density of from about 0.05 grams per cubic centimeter to about 0.15 grams per cubic centimeter, and more preferably from about 0.08 grams per cubic centimeter to about 0.13 grams per cubic centimeter. When densified in this manner, faster wicking of liquid throughout the composite pad structure results.

As another aspect of the present invention, the binder material is preferably a thermoplastic binder material, the insert pad is thermobonded, and the superabsorbent particles are held to the fibers by the binder material. Most preferably the binder material substantially continuously coats the fibers with the superabsorbent particles being applied to the fibers while the binder is still wet such that the binder adheres the fibers to the particles as the binder dries. Consequently, substantial areas of the superabsorbent particles do not have a binder coating and thus are exposed to more readily absorb liquid.

As a further aspect of the present invention, the binder material preferably comprises a binder with about 0.5 percent to about 30 percent free carboxyl groups. The free carboxyl groups strengthen the bonds between the fibers and the superabsorbent particles.

As a further aspect of the present invention, vertical wicking has been substantially improved by including a surfactant in the binder material.

As another aspect of the present invention, when the composite absorbent pad is included in an absorbent article, the composite pad may be wrapped in a nonwoven liquid permeable tissue.

Inasmuch as the bulk of the liquid discharged by a user wearing a diaper enters the front or target area of the diaper, it is possible to enhance the absorbency characteristics of the front portion of the diaper, relative to the back portion of the diaper, without significantly degrading the diaper's overall performance. In accordance with the present invention, the dispersion pad may extend co-extensively with substantially the entire length of the diaper and may, conventionally, assume an hourglass shape. In addition, the insert pad may be co-extensive with the dispersion pad, or may be much smaller in area than the dispersion pad with the insert pad being positioned at the target area of the diaper. For example, the insert pad may be from about ten to about eighty percent of the surface area of the liquid dispersion pad with the insert pad being positioned toward the front portion of the disposable diaper.

In addition, at least one, and preferably both, of the side edges of the insert pad may be spaced inwardly from the side edges of the liquid dispersion pad. For example, the side edges may be spaced apart at least about five millimeters and more preferably about 25 millimeters, to minimize leakage of the liquid from the insert pad at the side edge or edges of the absorbent article. Also, the insert pad typically extends approximately no more than about three-quarters of the length of the liquid dispersion pad.

As still another aspect of the present invention, hydrophilic fibers, such as from about five percent to about twenty-five percent by dry weight of the insert pad, may be included in the insert pad to enhance fluid wicking into the insert pad.

As a further aspect of the present invention, the insert pad abuts the dispersion pad at an interface surface. The fibers of the pads may be entangled at the interface surface to increase liquid wicking into the insert pad. In addition, the pads may be thermobonded individually and positioned together and may be thermobonded together at the interface. Thermoplastic containing fibers may be included in the dispersion pad for thermobonding purposes.

The insert pad typically has a taber stiffness of less than seven and, in certain embodiments of the invention, less than five. For products such as baby diapers, the insert pad typically has a basis weight of from about 250 grams per square meter to about 800 grams per square meter. A lower basis weight of as little as 150 grams per square meter is appropriate for products, such as adult incontinence pads, where a thinner cross-sectional dimension is required. The dispersion pad has a basis weight of from about 150 grams per square meter to about 350 grams per square meter.

It is accordingly one object of the present invention to provide an absorbent article, such as a disposable diaper, with enhanced liquid absorbency characteristics.

It is still another object of the present invention to provide an absorbent article utilizing superabsorbent particles in which the superabsorbent particles are bound within the article to minimize the possible migration of such particles from the diaper.

These and other object, features and advantages of the present invention will become apparent with reference to the following description and drawings.

DETAILED DESCRIPTION OF THE PREFERRED EMBODIMENTS

In accordance with the present invention, a composite absorbent pad or article includes an insert pad and a liquid dispersion pad with such composite pad being extremely useful for disposable absorbent products. These products are capable of absorbing significant quantities of water and other fluids, such as urine and body fluids. Such products include disposable diapers, sanitary napkins, incontinent pads, towels and the like. The use of composite pads of the present invention provides high absorbent capacity and products which can be relatively thin. In addition, products of good flexibility for comfort by the wearer can also be manufactured using composite pads of the present invention. In particular, the composite pad of the present invention is described below in connection with its use in a disposable diaper.

Figure 1:
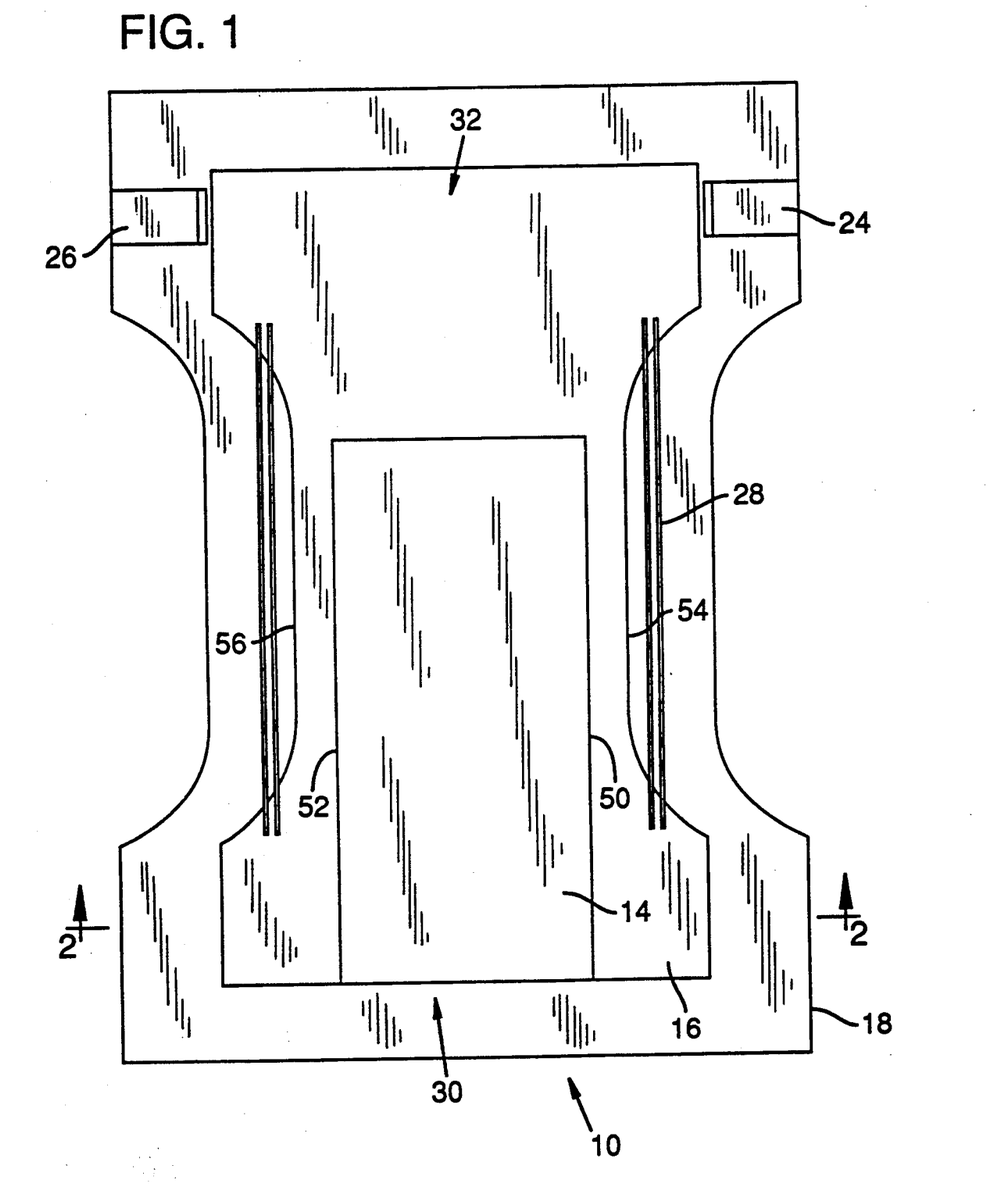
FIG. 1 is a top planned view of a disposable diaper having a composite absorbent pad structure comprising an insert pad and dispersion pad in accordance with the present invention with the diaper facing sheet removed for clarity.
Figure 2:
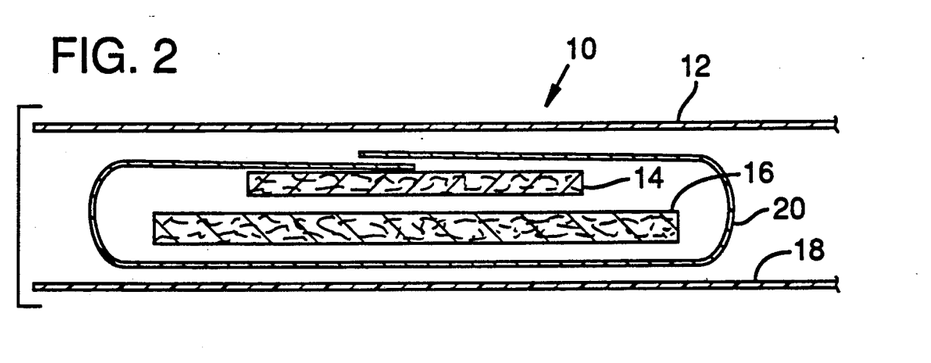
FIG. 2 is an exploded cross-sectional view of the disposable diaper of FIG. 1, with the facing sheet included, taken along lines 2—2 of FIG. 1.

With reference to FIGS. 1 and 2, a disposable diaper 10 may be comprised from (from top to bottom) a relatively liquid permeable or pervious top or facing sheet 12, an insert pad or layer 14 described in greater detail below, a liquid dispersion pad or layer 16 also described in greater detail below, and a liquid impermeable, pliable backing sheet 18. Optionally, the insert pad 14 and dispersion pad 16 are wrapped in an envelope tissue 20 which is typically of a basis weight of no greater than about sixty grams per square meter. Disposable diapers of this general structure, but without the composite insert pad 14 and dispersion pad 16 in accordance with the present invention, are known in the art.

In addition, typical disposable diapers include a fastening mechanism, such as tape tabs 24, 26, as is also known in the art. In addition, disposable diapers are frequently manufactured in the hourglass shape shown in FIG. 1 and have some mechanism, such as elastic bands 28, for gathering and at least partially sealing the diaper at the legs of the user when worn. Sealing mechanisms of any suitable type may be optionally included in the diaper construction of the present invention.

When the diaper of FIG. 1 is worn, the front portion of the diaper 30 is positioned toward the front of a user while the back portion of the diaper 32 is positioned against the buttocks and lower back of the user. The bulk of the liquid discharged by a user into a disposable diaper typically takes place in a target area toward the front portion of the diaper.

As previously mentioned, the facing sheet 12 is of any suitable relatively liquid permeable material. Nonwoven facing sheet materials are exemplary because such materials readily allow the passage of liquids to the underlying composite insert pad 14 and liquid dispersion pad 16. Specific examples of suitable facing materials include nylon, polyester, polypropylene and blends of these materials. Suitable commercially available facing materials include Cerex ® from James River Corporation, Reemay ® from Intertec Corporation, and Sonterra ® from DuPont Corporation. Any suitable facing material may be used which permits the passage of liquid through the facing material to the underlying composite pad structure. Typical backing sheet materials include films of polyethylene, polypropylene and polyester and blends of these materials along with nylon and polyvinyl chloride films. Again, any liquid impermeable backing sheet material may be used.

Referring again to FIG. 2, the insert pad 14 comprises a substantially bonded insert pad of fibers which are at least partially coated with binder material. The fibers are bound together by the binder material to form the substantially bonded insert pad. By substantially bonded, it is meant that the majority, and preferably substantially all, of the fibers are bound together at the contact points between the fibers. In addition, superabsorbent particles, or equivalently superabsorbent fibers, are adhered to the fibers by the binder material. The superabsorbent particles are present in a range of from about 10 percent to about 80 percent of the dry weight of the insert pad. Most preferably the superabsorbent particles are present in a range of from about 40 to 60 percent of the dry weight of the insert pad. In this latter range, the superabsorbent particles effectively absorb the liquid discharged into the disposable diaper without requiring excessive amounts of superabsorbent particles.

In addition, the insert pad 14 preferably is of a density of from about 0.05 grams per cubic centimeter to about 0.30 grams per cubic centimeter. In addition, the most preferred range of density is from about 0.18 grams per cubic centimeter to about 0.22 grams per cubic centimeter with about 0.20 grams per cubic centimeter being optimum for an insert pad having a superabsorbent particle concentration of about 50 percent. At densities below these ranges, the insert pad becomes thicker than desirable for a comfortable absorbent product. At densities above these ranges, the product is uncomfortably stiff, even when tenderized as explained below in connection with the manufacture of such pads. By densifying or concentrating the insert pad, improved wicking of liquid throughout the insert pad is achieved.

The basis weight of the insert pad 14 should be from about 250 to 800 grams per square meter. The taber stiffness of the insert pad is preferably no greater than about five for a comfortable product for a user. To achieve taber stiffness of these levels, the bonded insert pads are typically tenderized as explained below. One optimum diaper construction has an insert pad with a basis weight of about 500 grams per square meter and a taber stiffness from two to four.

The insert pad 14 may be comprised of a wide variety of fibers such as explained below, with discontinuous wood pulp fibers being a preferred fiber. In addition, as is also explained in greater detail below, the binder material may take a number of forms. However, the binder material is preferably of a heat fusible type such that the insert pad may be bonded or fused together by heating the binder material to its softening point. In addition, the fibers and binder adhere to the superabsorbent particles and hold these particles in place in the insert pad. In the preferred method of manufacturing the insert pad, the fibers are coated with liquid binder material with the superabsorbent particles being added while the binder material is still wet. During drying of the binder material, the fibers stick to the superabsorbent particles. With this approach, rather than having superabsorbent particles totally coated with binder material, portions of the superabsorbent particles will be exposed for more effective liquid absorption. Thereafter, the superabsorbent particles are more firmly locked in place by heat bonding the insert pad. Heat bonding may be accomplished before or after the binder material is allowed to dry.

In addition, it is preferable that the binder material substantially continuously coat the fibers. By producing fibers as explained below, such as by recirculating the fibers in air as the binder is applied, a sufficient amount of binder can be applied to substantially continuously coat the fibers. In addition, substantial quantities of binder can be applied beyond the amounts needed to continuously coat the fibers. As a result, sufficient binder is present to securely hold the superabsorbent particles in place. In addition, relatively strong fiber-to-fiber bonds are achieved following heat fusing.

To improve the wicking characteristics of the insert pad 14, a relatively small amount of hydrophilic fibers, such as untreated (that is nonbinder coated) wood pulp fibers may be included in the insert pad. For example, five to 25 percent of such fibers may be included. Although the inclusion of untreated fibers does weaken the fiber-to-fiber bonding to a limited extent, the treated fibers may contain sufficient binder to substantially overcome this drawback. Although the exact theory and mode of operation cannot be determined, it is believed that the untreated fibers provide a wicking path for conducting liquid to the interior of the insert pad 14 and thus to superabsorbent particles that are spaced from the surface of this insert pad.

By assembling the composite structure comprised of the insert pad 14 and liquid dispersion pad 16, either prior to thermobonding of the insert pad 14 or thereafter, and then heating the composite structure sufficient to soften the binder material, some of the binder material in insert pad 14 at the interface 40 between the insert pad and dispersion pad, will assist in fusing pads 14 and 16 together at the interface. This helps provide a stronger composite structure. In addition, the liquid dispersion pad 16 may include heat fusible binder containing fibers, such as thermoplastic fibers or fibers coated at least in part with a binder material. When such fibers are included and a composite structure is heated, some bonding again takes place at the interface 40. Typically, relatively small amounts of binder containing fibers would be included in the dispersion pad 16, such as less than about 20 percent of binder material by weight.

In addition, the insert pad 14 and liquid dispersion pad 16 may have fibers which are entangled at the interface to enhance the wicking of liquid into the insert pad 14. Entanglement of these fibers may for example, be achieved by compressing the two pads together. In addition, heat bonding of the pads also enhances the liquid transfer between the pads. The dispersion pad and insert pad may be separately formed and then assembled into a composite pad, with thermobonding and densification of the pads being accomplished before assembly. Alternatively, the two pads may be formed and simultaneously thermobonded.

The liquid dispersion pad 16 may also be made of any suitable material, with discontinuous fiber material being preferred. The fibers included in the liquid dispersion pad 16 may be similar to the fibers included in the insert pad 14. However, the fibers included in the dispersion pad 16 are typically not treated with a binder material. However, as mentioned above, some binder containing fibers may be used to provide a bonded dispersion pad. Because of the availability and relatively inexpensive nature of wood pulp fibers, such fibers typically make up all or substantially all of the dispersion pad 16.

In general, the dispersion pad 16 has been observed to improve the wicking and dispersion of liquid throughout the insert pad 14. The insert pad typically carries or holds the bulk of the liquid that is discharged into the disposable diaper due to the superabsorbent particles contained therein.

It has also been found that the rewetting characteristics of the disposable diaper are substantially improved if the liquid dispersion pad is densified somewhat. Preferably, the dispersion pad 16 is densified to a density of from about 0.05 grams per cubic centimeter to about 0.15 grams per cubic centimeter, with densities from about 0.08 to 0.13 grams per cubic centimeter being preferred. At a density beyond about 0.15 grams per cubic centimeter, the rewet characteristic of the dispersion pad is not significantly improved. In addition, the dispersion pad becomes undesirably stiff for a comfortable product. In addition, the basis weight of the dispersion pad should be about 150 to 350 grams per square meter. In our desirable constructions, the basis weight of the dispersion pad was about 250 grams per square meter such that the dispersion pad would provide cushioning to a user.

The dispersion pad is typically compressed, as between a pair of rollers, to achieve the desired density. In this case, and assuming untreated wood pulp fiber is the fiber included in the dispersion pad, some hydrogen bonding of the fibers takes place.

In addition, the vertical wicking characteristics of the composite structure of the insert pad and dispersion pad is improved by adding a surfactant to the binder material. For example, assuming a Synthemul 40-504 thermoplastic binder is used in accordance with Example 1, the vertical wicking characteristics of the insert pad 14 was improved by approximately one-third when one percent surfactant (for example OTS surfactant as is explained in this example) is added. This particular binder comprises an emulsion of particles of binder in a carrier fluid. Another version of this binder identified as 97883, also from Reichhold Chemical Corporation, has smaller particles in a carrier fluid. It has been found that the vertical wicking rate of the composite structure was enhanced by using the binder comprised of these smaller particles. In addition, the inclusion of hydrophillic fibers, such as wood pulp, in the insert pad enhanced the vertical wicking characteristic of the insert pad. From five to about twenty-five percent hydrophilic fibers are typically included. For example, a binder treated fiber (e.g, 12.5 percent 40-504 latex by weight; 50 percent superabsorbent particles (SAP) by weight; and 37.5 percent fiber by weight) can be blended with an additional 10 and 15 percent by weight untreated (non-binder coated) wood pulp fibers to improve vertical wicking by about 42 percent. In addition, instead of using IM 1000 superabsorbent particles from Hoechst Celanese Corporation, improved wicking should also result from the use of IM 3500 superabsorbent particles, also from this company.

TABLE I
RESULTS:

| Latex | % SAP | Comment | Basis Wt. g/m 2 | Dens. g/cc | Vertical wicking rate (Sec. at 1.5") |
|---|---|---|---|---|---|
| 12.5% 40-504 + 1% ots | 50 | | 791 | 0.227 | 33 |
| 12.5% 97883 + 1% ots | 50 | | 773 | 0.203 | 26 |
| 12.5% 40-504 | 50 | Control | 789 | 0.234 | 50 |
| 12.5% 40-504 | 50 | Tenderized control | 638 | 0.222 | 49 |
| 11.25% 40-504* | 45 | Tenderized | 657 | 0.223 | 29 |
| 10.6% 40-504** | 42.5 | Tenderized | 673 | 0.223 | 29 |

In the above table, * refers to an insert pad with a blend of 10% untreated (nonbinder coated) wood pulp fibers in the pad and ** refers to a pad with 15% untreated wood pulp fibers. In addition, tend. refers to tenderizing the pad as explained in connection with the pad manufacturing description below. In general, tenderization did not appear to affect the vertical wicking characteristic of the insert pads.

In determining the vertical wicking properties of the insert pads 14, two inch wide strips of the test sample material were supported in a vertical orientation with one-half inch of the lower end of the test sample inserted into a one percent saline solution. The vertical wicking identified in Table I is the seconds required for the liquid to wick upwardly a distance of 1½ inches from the surface of the liquid in which the end of the test sample is immersed. The insert pad should have a vertical wicking of no more than about thirty-five seconds at 1.5" (i.e., the wicking rates should be no more than about twenty-three seconds per inch of vertical height).

Disposable diapers comprising the absorbent structure of the present invention with an insert pad and dispersion pad may be made by using conventional diaper making techniques. However, the wood pulp fiber web or core which is typically used in conventional diapers is replaced with the absorbent core structure of the present invention.

Figure 4:
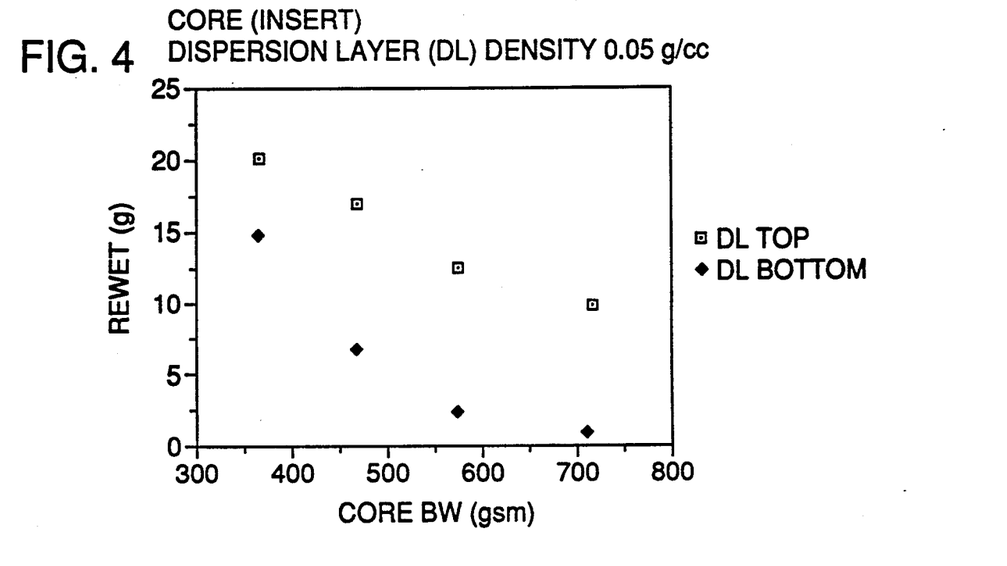
FIG. 4 is a chart illustrating the rewet characteristics of disposable diapers in accordance with the invention with the insert pad overlying the dispersion pad and which compares these results with the results obtained with the dispersion pad overlying the insert pad.

The chart of FIG. 4 depicts the rewet characteristics of the absorbent article of the present invention as a function of basis weight of the insert pad and also compares the rewet characteristics of the article with the insert pad on top of the dispersion pad to the rewet characteristics with the insert pad beneath the dispersion pad. In the chart of FIG. 4, the dispersion pad was densified to a density of 0.05 grams per cubic centimeter.

As is apparent from this chart, the rewet characteristics of the article is substantially improved at all of the illustrated basis weights when the insert pad is positioned over the dispersion layer in comparison to the case where the insert pad is positioned underneath the dispersion layer.

Figure 3:
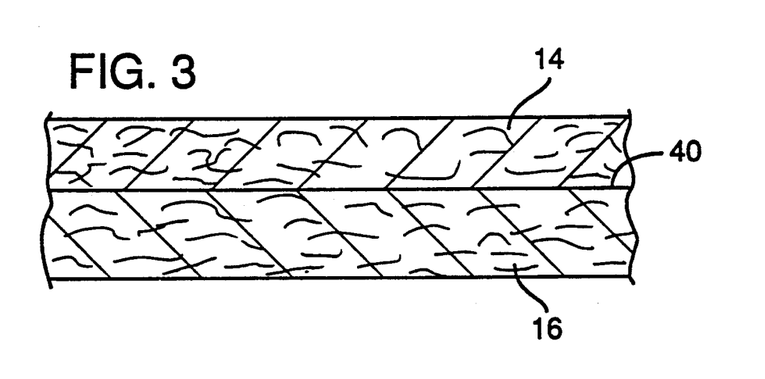
FIG. 3 is an enlarged view of the composite insert pad and dispersion pad of the present invention.

In performing this rewet testing, a six inch diameter test pad structure was constructed. This test pad included two layers comparable to the insert pad and dispersion pad shown in FIG. 3. Eighty grams of synthetic urine was discharged through a funnel to the center of the diaper with the discharge tip of the funnel being positioned 1.5 inches above the bench top on which the diaper is supported. After ten minutes, pre-weighed filter papers were positioned on the center of the wet area of the diaper with a 1.0 pound per square inch weight being placed on the filter papers. The weight was placed exactly centered on the filter papers and was released slowly. After two minutes, the weight was removed and the filter papers were weighed. The rewet is defined as the weight of the wet filter papers in grams minus the weight of dry filter papers in grams. The average results in grams of at least five replications is typically included in the data.

Figure 5:
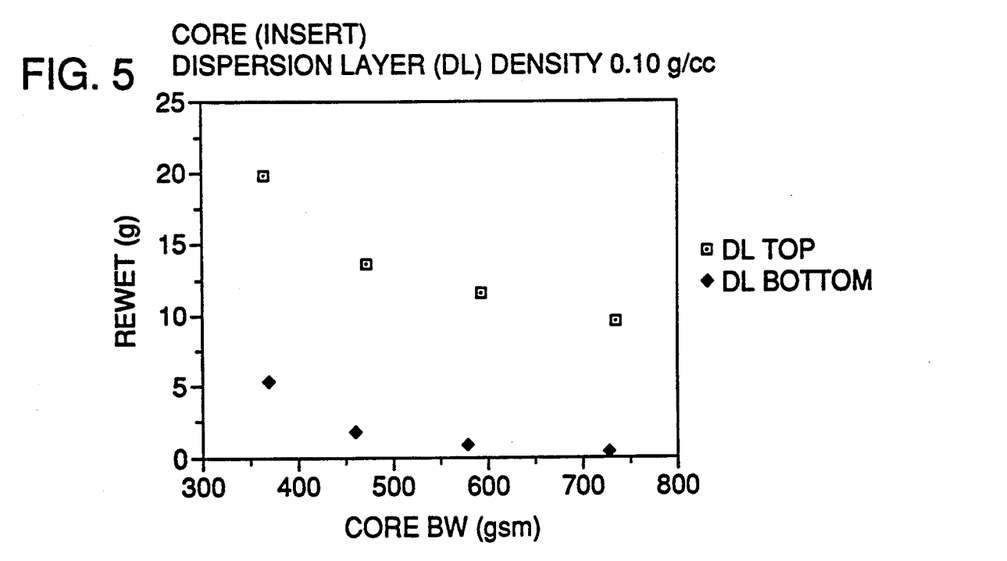
FIG. 5 is a chart like the chart of FIG. 4 with the dispersion layer at a higher density than in the FIG. 4 chart.

The chart of FIG. 5 is similar to the chart of FIG. 4 except that the dispersion layer has been densified to 0.10 grams per cubic centimeter. As illustrated in FIG. 5, the use of a higher density dispersion layer significantly improved the rewet characteristics of the disposable diaper.

Inasmuch as rewetting is an indication of tha wetness against a user's skin following discharge of liquid into the article, it is desirable to minimize this rewetting. To the extent that rewetting occurs, skin irritation and rash can increase, particularly if diapers are not immediately changed when wet.

With reference again to FIG. 1, the illustrated insert pad 14 overlies less than the full area of the underlying dispersion pad 16. Although the insert pad 14 may be co-extensive, or even larger than, the area of the dispersion pad, desirable fluid absorbing properties are also achieved if the insert pad is positioned more toward the front 30 of the diaper and thus in the target area. The preferred form of insert pad is sized to overlie approximately 10 to 80 percent of the area of the dispersion layer, and more particularly approximately 20 to 60 percent of this area. In addition, the insert pad has a length, measured in a direction from the top to bottom edge of the diaper of approximately one-half to three-fourths of the length of the underlying dispersion pad. In addition, at least one, and preferably both, of the respective side edges 50, 52 of the insert pad are spaced inwardly from the respective adjacent side edges 54, 56 of the dispersion pad 16. Preferably, the spacing between these respective side edges is not less than about 1 millimeter and most preferably no less than about 5 millimeters. This spacing minimizes the possible leaking of liquid from the insert pad to the sides of the disposable diaper and therefore improves the product.

The insert pad and dispersion pad may be of any relative thickness. However, to reduce the bulk of these disposable diapers, it is generally desirable to keep these pads as thin as possible while still providing enhanced fluid absorption characteristics. As one specific example, the insert pad may be constructed with a basis weight of about 500 grams/sq.meter, a 50 percent superabsorbent particle concentration by weight, and a density of 0.2 grams per cubic centimeter. The taber stiffness of the insert pad was from two to four as determined by TAPPI standard test method T 489. TAPPI refers to the Technical Association of Pulp and Paper Industry. From T 489, the Taber stiffness (gm cm) is the bending movement necessary to deflect the free end of a vertically clamped specimen (38 mm wide) 15° from its centerline when the load is applied 50 mm away from the clamp. In addition, in this example, the dispersion may be constructed with a basis weight of approximately 250 grams/sq.meter and at a density of about 0.1 grams per cubic centimeter.

As discussed above, the insert pad 14 is a fiber product best comprised of treated discontinuous synthetic and/or natural fibers. The term discontinuous fibers refers to fibers of a relatively short length in comparison to continuous fibers treated during an extrusion process used to produce such fibers. The term discontinuous fibers also includes fiber bundles. The term individual fibers refers to fibers that are comprised substantially of individual separated fibers with at most only a small amount of fiber bundles. Chopped or broken synthetic fibers also fall into the category of discontinuous fibers. Although not limited to any particular type of fiber, the synthetic fibers commonly are of polyethylene, polypropylene, acrylic, polyester, rayon and nylon. Discontinuous fibers of inorganic and organic material, including cellulosic fibers are also included. The natural fibers may likewise be of a wide variety of materials, with chopped silk fibers, wood pulp fibers, begasse, hemp, jute, rice, wheat, bamboo, corn, sisal, cotton, flax, kenaf and the like, and mixtures thereof, being several examples.

Wood pulp fibers can be obtained from well-known chemical processes such as the kraft and sulfite processes. Suitable starting materials for these processes include hardwood and softwood species, such as alder, pine, douglas fir, spruce and hemlock. Wood pulp fibers can also be obtained from mechanical processes, such as ground wood, refiner mechanical, thermomechanical, chemi-mechanical, and chemi-thermomechanical pulp processes. However, to the extent such processes produce fiber bundles as opposed to individually separated fibers or individual fibers, they are less preferred. However, treating fiber bundles is within the scope of the present invention. Recycled or secondary wood pulp fibers and bleached and unbleached wood pulp fibers can also be used. Details of the production of wood pulp fibers are well-known to those skilled in the art. These fibers are commercially available from a number of companies, including Weyerhaeuser Company, the assignee of the present patent application.

For purposes of convenience, and not to be construed as a limitation, the following description proceeds with reference to the treatment of individual chemical wood pulp fibers. The treatment of individual fibers of other types and obtained by other methods, as well as the treatment of fiber bundles, can be accomplished in the same manner.

When relatively dry wood pulp fibers are being treated, that is fibers with less than about 10 to 12 percent by weight moisture content, the lumen of such fibers is substantially collapsed. As a result, when binder materials, in particular latex binder materials, are applied to these relatively dry wood pulp fibers, penetration of the binder into the lumen is minimized. In comparison, relatively wet fibers tend to have open lumen through which binder materials can flow into the fiber in the event the fiber is immersed in the binder. Any binder that penetrates the lumen contributes less to the desired characteristics of the treated fiber than the binder which is present on the surface of the fiber. Therefore, when relatively dry wood pulp fibers are treated, less binder material is required to obtain the same effect than in the case where the fibers are relatively wet and the binder penetrates the lumen.

Binders used to treat the fibers broadly include substances which can be applied in liquid form to entrained fibers during the treatment process. These binder materials are preferably of the type which are capable of subsequently binding the fibers produced by the process to one another or to other fibers during the manufacture of webs and other products using the treated fibers. Most preferably these binders comprise organic polymer materials which may be heat fused or heat cured at elevated temperatures to bond the fibers when the fibers are used in manufacturing products. Also, the binder must be of a type which is suitable for the purpose of adhering the fibers to superabsorbent particles.

Suitable binders include polymeric materials in the form of aqueous emulsions or solutions and nonaqueous solutions. To prevent agglomeration of fibers during the treatment process, preferably the total liquid content of the treated fibers during treatment, including the moisture contributed by the binder together with the liquid content of the fibers (in the case of moisture containing fibers such as wood pulp), must be no more than about 45 to 55 percent of the total weight, with a 25 to 35 percent moisture content being more typical. Assuming wood pulp is used as the fiber, the moisture contributed by the wood pulp can be higher, but is preferably less than about 10 to 12 percent and more typically about six to eight percent. The remaining moisture or liquid is typically contributed by the binder. These polymer emulsions are typically referred to as "latexes." In the present application, the term "latex" refers very broadly to any aqueous emulsion of a polymeric material. The term solution means binders dissolved in water or other solvents, such as acetone or toluene. Polymeric materials used in binders in accordance with the present method can range from hard rigid types to those which are soft and rubbery. Moreover, these polymers may be either thermoplastic or thermosetting in nature. In the case of thermoplastic polymers, the polymers may be a material which remains permanently thermoplastic. Alternatively, such polymers may be of a type which is partially or fully cross-linkable, with or without an external catalyst, into a thermosetting type polymer. As a few specific examples, suitable thermoplastic binders can be made of the following materials:

ethylene vinyl alcohol
polyvinyl acetate
acrylic
polyvinyl acetate acrylate
acrylates
polyvinyl dichloride
ethylene vinyl acetate
ethylene vinyl chloride
polyvinyl chloride
styrene
styrene acrylate
styrene/butadiene
styrene/acrylonitrile
butadiene/acrylonitrile
acrylonitrile/butadiene/styrene
ethylene acrylic acid
polyethylene
urethanes
polycarbonate
polyphenylene oxide
polypropylene
polyesters
polyimides Surfactants may also be included in the liquid binder as desired. Other materials may also be mixed with the liquid binder to impart desired characteristics to the treated fibers. For example, particulate material, such as pigments, may also be included in the binder for application to the fibers. In addition, superabsorbent particulate materials are adhered to the fibers to provide desired functional characteristics. The solid particulate materials are applied to a binder wetted surface of the fibers and are then adhered to the fibers by the binder as the binder dries. In this case, heat curing or heat fusing of the binder is not required to adhere the particles to the fibers. Thus, the superabsorbent particles are not coated with the binder, which could interfere with their optimum capacity to absorb liquid.

The superabsorbent particulate materials are granular or powdered materials which have the ability to absorb liquids, including body fluids. Equivalently, superabsorbent fibers may be used. These superabsorbents are generally hydrophilic polymeric materials. Superabsorbents are defined herein as materials which exhibit the ability to absorb large quantities of liquids, i.e., in excess of 10 to 15 parts of liquid per part thereof. These superabsorbent materials generally fall into three classes, namely, starch graft copolymers, cross-linked carboxymethylcellulose derivatives and modified hydrophilic polyacrylates. Without limiting the generality of the term superabsorbent, examples of superabsorbents include carboxylated cellulose, hydrolyzed acrylonitrile-grafted starch, acrylic acid derivative polymers, polyacrylonitrile derivatives, polyacrylamide type compounds and saponified vinyl acetate/methyl acrylate copolymers. Specific examples of superabsorbent particles are marketed under the trademarks "Sanwet" (supplied by Sanyo Kasei Kogyo Kabushiki Kaisha) and "Sumika Gel" (supplied by Sumitomo Kagaku Kabushiki Kaisha).

Figure 6:
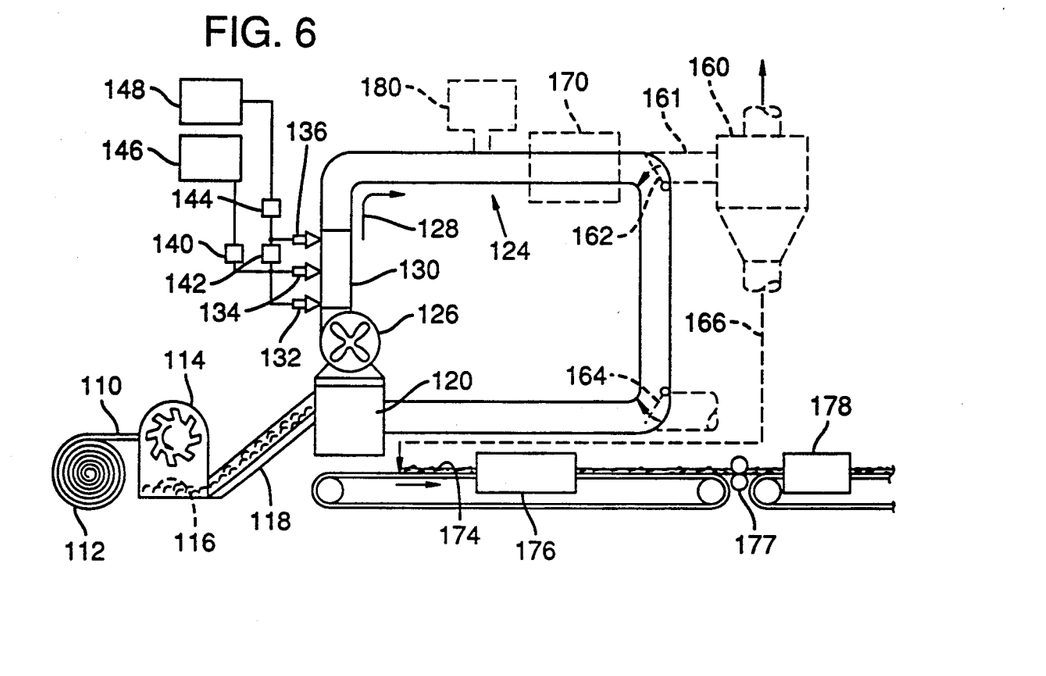
FIGS. 6 and 7 are schematic illustrations of forms of an apparatus in which an insert pad and dispersion pad in accordance with the present invention can be manufactured.

FIG. 6 shows an apparatus suitable for making the insert pad 14 and/or dispersion pad 16. In this apparatus, a sheet 110 of fibrous material, such as chemical wood pulp, is unrolled from a roll 112 and delivered to a refiberizing apparatus, such as a conventional hammer mill 114. The sheet 110 is readily converted into individual fibers 116 within the hammer mill. These individual fibers are delivered, as by a conveyor 118, to a fiber loading zone 120 of a fiber treatment apparatus. In the case of a continuous process, fibers 116 are continuously delivered to the zone 120. In a batch or semi-batch process, fibers are loaded at zone 120 at intervals.

Loading zone 120 forms part of a fiber treatment conduit 124. The illustrated conduit 124 comprises a recirculating loop. A blower or fan 126 in the loop 124 is positioned adjacent to the fiber loading zone 120. Blower 126 is capable of moving a gaseous medium, such as air, at a velocity and volume sufficient to entrain the fibers which have been loaded into zone 120. The entrained fibers circulate in a direction indicated by arrow 128 through the loop and pass through the loading zone 120 and blower 126 each time the loop is traversed.

The velocity of air traveling in the loop is preferably set at a level where solids are uniformly dispersed and transported by the air flow. In addition, the velocity is preferably established at a level which is sufficient to avoid saltation, that is the dropping of solids or liquids from a horizontal air stream. As a specific example, when Type NB316 chemical wood pulp, available from Weyerhaeuser Company, was used as the fiber, a velocity of 5,000 feet per minute worked extremely well for treatment of these fibers. However, this velocity can be varied and adjusted for optimum results.

Also, the ratio of the volume of air per pound of entrained fiber is variable over relatively large ranges. One suitable example is 23.4 ft$^3$ of air per pound of fiber. As another example, 11.7 ft$^3$ of air per pound of fiber produced equivalent results.

The entrained fibers traveling in the loop pass one or more binder material application zones, with one such zone being indicated in FIG. 6 at 130. This binder material application zone 130 forms a part of the conduit 124. A mechanism is provided at the binder application zone for applying a liquid binder solution to the entrained fibers. When the insert pad 14 is being formed, plural nozzles, in this case nozzles 132, 134 and 136, may be used to apply the liquid binder material. These nozzles produce an atomized spray or mist of binder drops which impact and coat the fibers as the fibers pass the nozzles.

Plural valves 140, 142 and 144 are operated to control the flow of liquid binder material to the respective nozzles 132, 134 and 136. In the illustrated configuration, a first liquid binder material from a tank or other source 146 is delivered to the three nozzles 132, 134 and 136 when valves 140 and 142 are opened and valve 144 is closed. As the fibers recirculate through the conduit 124, and each time they pass the nozzles, an additional amount of the first liquid binder material is applied. Different surfaces of the fibers are exposed to the nozzles 132, 134 and 136 as the fibers travel through the material application zone 130. After the desired amount of the first liquid binder material is applied, the valve 140 is closed. If desired for a particular application, a second liquid binder material from a tank or other source 148 may also be applied to the fibers. With valves 142 and 144 open and valve 140 closed, this second liquid binder material is applied to the fibers through each of the nozzles 132, 134 and 136. In addition, the two liquid binder materials may be simultaneously applied, at successive locations in zone 130. For example, the valve 142 may be closed and valve 144 opened so that the first liquid binder material is applied through nozzles 132, 134 and the second liquid binder material is applied through nozzle 136. More than two types of liquid binder materials may be applied by adding additional binder sources and suitable valving and nozzles.

In general, the material application zone 130 typically ranges from two to one hundred feet long, with longer application zones allowing the application of binder over a longer period of time during passage of fibers through the material application zone. Also, longer material application zones facilitate the use of more nozzles spaced along the length of the zones.

The nozzles 132, 134 and 136 are commercially available and produce a fine mist of droplets. Typically, these nozzles provide a fan spray. Any suitable nozzles may be used, but it is desirable that the nozzles not produce a continuous stream of liquid binder material, but instead produce droplets or a mist of such material. The nozzles are typically spaced apart from three to four feet along the length of the conduit, although they may be closer or further apart as desired.

Virtually any amount of binder material may be applied to the entrained fibers. However, it has been found that the application of binder must be at a minimum of about seven percent of the dry weight of the combined fibers and binder in order for the fibers to have a substantially continuous sheath or coating of the binder material. If the fibers lack a continuous coating, it becomes more difficult to adhere significant amounts of superabsorbent particulate material to the binder in the manner explained below. In fact, a much higher percentage of binder than this minimum is preferably used to adhere these particles and the fibers. Also, exposed portions of the core fiber, that is surface areas of the fiber not coated with the binder, lack the desired characteristics of the binder. For example, if a hydrophobic binder is used to cover a water absorbing cellulose material, failure to completely enclose the material with the coating leaves exposed surfaces of the fiber which can absorb water. Also, any uncoated areas on the fibers would not bond to other untreated fibers during subsequent heat bonding of the treated and untreated fibers.

It has also been found that, with a binder concentration of about 10 percent by dry weight of the weight of the fiber and binder combination, the fibers, when heat fused, will bond somewhat strongly to other fibers coated in a similar manner, but less strongly to untreated fibers. The resulting bond strength is similar to the strength achieved when fibers coated with a 40 percent by dry weight binder amount are mixed with untreated fibers in a ratio of one part treated fiber to three parts untreated fiber. A binder concentration by dry weight of the combined binder and fibers of from 30 percent to 50 percent has proven extremely suitable for use in mixing with other fibers, heat bonding, and use in forming products such as absorbent pads.

Binder concentrations in excess of 50 percent, for example 90 percent or more, can be achieved utilizing the present invention. To achieve these extremely high binder concentrations, one preferred approach is to apply a first amount of the binder material to the entrained fibers, continue to recirculate the fibers until this first layer or coating of binder material is substantially dry, and then apply a second coating of the binder material. Third, fourth and subsequent coatings can be applied to the entrained fibers as necessary to achieve the desired level of binder material.

Following the application of the liquid binder material to the fibers and the addition of super absorbent particulate material as explained below, the fibers may be retained in the loop until they have dried. The recirculation of the fibers may then be stopped and the fibers removed at the loading zone 120, which then functions as a fiber removal location. However, in the FIG. 1 apparatus, a cyclone separator 160 is selectively connected by a conduit section 161 and a gate valve 162 to the conduit 124. At the same time a valve 164 is opened to allow air to enter the loop 124 to compensate for air exiting through the separator 160. With the separator in the loop, the entrained fibers are collected in the separator and then removed from the separator at a fiber removal outlet 166. A substantial majority of the fibers processed in this manner are unbonded to one another by the binder material. By substantial majority, it is meant that at least about 70 percent of the fibers remain unbonded. More specifically, in tests conducted as of this time, the resulting treated fibers are substantially unbonded, meaning that approximately 95 percent of the treated fibers have been found to be unbonded to one another by the binder material. However, plural fibers are bonded to the superabsorbent particles.

An optional means for heating the binder coated fibers may be included in conduit 124. For example, heated air may be blended with the air flowing through the conduit. Similarly, a heater 170 may be included in conduit 124 for heating the fibers. This added heat accelerates the drying of the liquid binder and adhered superabsorbent particles. In the event a thermoplastic heat fusible binder is used, the fibers are preferably heated above the film forming temperatures of the binder and below the hot tack temperature at which the binder becomes tacky so that the binder coated fibers may subsequently be heat fused during processing of the fibers into products. Also, if a thermoset heat fusible binder is used, the fiber temperature is preferably maintained below the curing temperature of the binder so that the binder coated fibers may be subsequently heat cured during the processing of the binder coated fibers into products.

The fibers are preferably not heated prior to the application of the binder material. It has been found that heating the fibers results in elevated temperatures at the binder application zone 130. These elevated temperatures cause some of the binder to at least partially dry (coalesce) before reaching surfaces of fibers passing through the binder application zone 130. The solidified binder tends to either not adhere, or only adhere weakly, to the fibers. In addition, droplets of binder which impinge heated fibers tend to dry in globules on the fibers, rather than spread across the surface of the fibers to provide a substantially continuous uniform coating thereon.

The dried fibers from outlet 166 of the cyclone separator 160 may be deposited onto a conveyer 174. If hydrophillic fibers are to be included in the insert pads 14, they are typically mixed with the binder treated fibers with the mixed treated and untreated fibers being deposited onto a conveyor. These fibers may then be heated in a thermobonder 176 and thereafter compressed to the desired density, as by passing the bonded web through calendar rolls 177. Following thermobonding, to reduce the stiffness of the webs, they may be "tenderized" such as by the use of a mechanism which mechanically breaks up some of the bonds in the web. The web still remains substantially bonded, however. As one example, the webs may be passed through the nips of cross machine direction and machine direction corrugators 178 to reduce their stiffness. The stiffness can be controlled by adjusting the clearance between the nips. Although not limited to a specific approach, examples of suitable corrugators and tenderizing procedures are disclosed in U.S. Pat. No(s). 4,559,050; 4,596,567 and 4,605,402, which are hereby incorporated by reference. By tenderizing the insert, the desired taber stiffness, such as less than 7 and more preferably no greater than about 5, can be achieved.

The dispersion pad 16 may be formed in any suitable manner, such as by air laying a web onto a conveyor. The dispersion pad may be densified by, for example, compressing the pad between rollers to the desired density. The dispersion pad forming web may also be compressed against the insert pad forming web to entangle the fibers at the interface between these webs. Also, if the dispersion pad has thermoplastic containing fibers, it may be bonded in a thermobonder separately from, or simultaneously with, the thermobonding of the insert pad forming web.

Figure 7:
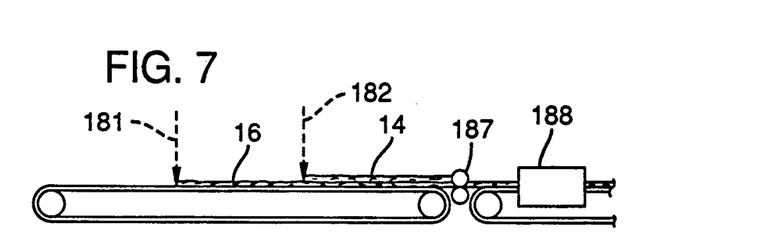

A particular example method is illustrated by FIG. 7. First the dispersion pad 16 is formed by air laying 180 a web onto a conveyor. Subsequently, the insert pad 14 is air layed 182 onto the dispersion pad 16. Both pads may be air layed using apparatus of the type shown in FIG. 6. The superposed pads are passed through a pair of nip rolls 187 to mechanically compress the pads together. Thereafter, the combined pads are passed through a thermobonder 188 so that the two pads are bonded together simultaneously with the bonding of the insert pad fibers.

As shown in FIG. 6, the superabsorbent particles are added to the loop 124, such as at the fiber loading zone 120. The particles may also be added to the loop 124 from a supply housing 180, using a feed screw metering device or other conventional injection mechanism. Preferably, the particles are added after the fibers have been wetted with the binder material. Consequently, the particles will not be covered with the binder material, which could interfere with the desired attributes contributed by the particles. These particles contact the wet binder material on the surfaces of the fibers and stick to the binder material. As the binder material dries, the particles remain stuck to the surface of the treated fibers. Although lower concentrations are effective in binding particles to fibers, it has been found that relatively high levels of binder concentrations, for example 20 percent or more of the dry weight of the binder, fiber and particles produces the best adhesion of particles to the fibers. A 50 percent binder concentration would perform better at adhering particles to the fibers than a 20 percent binder concentration in many applications. Also, higher binder concentrations generally produce stronger bonds when the fibers are subsequently thermobonded.

The operation of the apparatus of FIG. 6 is described in greater detail in U.S. patent application serial number 07/326,199 (Neogi, et al) filed Mar. 20, 1989, which is hereby incorporated by reference. The Neogi et al patent also shows other suitable means for incorporating binder material and particles onto the fibers.

The following examples will serve to more specifically illustrate the method of the present invention, although it is to be understood that the invention is not limited to these examples.

EXAMPLE 1

A bleached Kraft Southern Pine cellulose fiber pulp sheet (NB-316 from Weyerhaeuser Company) was fiberized in a hammer mill. In addition, 1075 grams of the fiberized fluff was then air entrained in a recirculating conduit. After 20 seconds of air entrainment, sufficient Primacor 4990 ethylene acrylic acid copolymer solution (as a 20 percent solids dispersion) was sprayed onto the air entrained fiber over a period of eight minutes. Primacor is a hydrophobic, somewhat oleophilic thermoplastic binder. Primacor 4990 is available from Dow Chemical Corporation. In addition, a surfactant material was added to the Primacor for application with the binder. In this specific example, Aerosol OT-S Dioctyl Sodium Sulfosuccinate 70.2 percent TS, available from American Cyanamid Corporation, was used as the surfactant material. In this example, 1.74 percent surfactant was included, based on the Primacor solids.

The loop was then opened and a desired amount of superabsorbent particles was deposited onto the damp fluff. A specific example of superabsorbent particles is Sanwet IM-1000, available from Celanese Corporation. The coated fiber was then recirculated for twenty seconds prior to removal from the loop. Recirculation of the materials through the loop mixed the particles with the still wet and entrained fibers. Continued circulation of the fibers resulted in partial drying of the binder and adhesion of the particles to the fibers. The still somewhat wet coated fibers were then deposited in a loose pile and air dried at room temperature for 24 hours. With percentages expressed as the percent of the dry weight of the total weight of the fiber, binder and superabsorbent particle combination, a number of samples were prepared in this manner, including:

1% Primacor 20% superabsorbent particles
2% Primacor 40% superabsorbent particles
2% Primacor 50% superabsorbent particles
5% Primacor 50% superabsorbent particles
10% Primacor 50% superabsorbent particles
15% Primacor 20% superabsorbent particles
20% Primacor 50% superabsorbent particles With at least about a 7% binder concentration (dry weight of binder as a percent of the dry weight of the binder and fiber only), a substantially continuous binder coating of the fibers occurred. Even though wood fibers are of irregular cross-section and thus more difficult to coat than surfaces with a regular cross-section or smooth surface, the resultant fibers had a uniform continuous coating of binder. Also, approximately 95 percent of the fibers were unbonded to one another by the binder material, although fibers were bonded to the superabsorbent particles. The dried fiber was then easily air laid in a laboratory pad former. Observations of the resulting pads confirmed that the binder adhered the fibers to the superabsorbent particles, however very little adhesion occurred at binder concentrations below about seven percent. More specifically, it has been found that a binder concentration of 7 percent will adhere some particulate material to the fibers, but at binder concentrations of 20 percent and higher of the total dry weight of the binder and fiber, much better adhesion occurs. Also, a very uniform distribution of superabsorbent particles was present in the resulting web and enhanced the water absorbing characteristics of the web.

It should be noted that the use of surfactants is desirable in many applications, but not mandatory. When used, the vertical widening of the insert pads 14 were enhanced.

A wide variety of other binders have also been tested, including Synthemul 40-800 and 40-850 emulsions, available from Reichhold Chemical Corporation. Cellulose fibers having 5 percent, 7 percent, 10 percent, 20 percent, 30 percent and 50 percent by dry weight Synthemul 40-800 coating have been manufactured. Again, it is only at levels of about 7 percent that a continuous coating of the fibers is achieved. At 5 percent, the binder material was present as non-interconnected areas or blobs on the surface of the fibers. These percentages are the percent of dry weight of the fiber and binder combination which is the binder. In a recirculating system, to achieve higher percentages of the binder concentration, the fibers were recirculated in the loop during liquid binder application for a longer time. Synthemul is a more hydrophilic binder than Primacor. Also, Elvace 40-712, available from Reichhold Chemical Corporation, an ethylene vinyl acetate, has also been tested as having a number of other binder materials. Superabsorbent particles in the desired concentration can be adhered by the binding to these fibers. These tests have all confirmed that fibers coated with a substantially continuous coating of binder material and adhered to superabsorbent particles can be produced in accordance with the method of the present invention.

Preferably the binders are of a polymeric heat bondable type (for example thermoset or thermoplastic binders) so that they may be subsequently heat bonded, with or without other fibers, in manufacturing a product. However, inorganic materials, such as liquid sodium silicate, in an amount sufficient to provide a substantially continuous coating of the fibers may also be used to adhere particles to the fibers. Although such materials are not used in binding fibers together during subsequent processing, they are capable of binding particles to the fibers and thus in this sense can be called binders. In addition, these materials, when coated on the fibers, add characteristics to the fibers. For example, silicon dioxide increases the wetability of the fibers.

EXAMPLE 2

It has been found that better adhesion of superabsorbent particles to fiber is achieved if the binder is of a type which has free carboxyl groups, such as from about 0.5 to 30 percent the carboxyl groups. In addition, the higher the percentage of free carboxyl groups in the binder, the greater the observed strength of adhesion of the superabsorbent particles to the fibers. Fibers with adhered superabsorbent particles were manufactured as explained above in connection with Example 1. A comparison of the strengths of adhesion of superabsorbent particles was made with Primacor as a binder and with Synthemul 40-504, from Reichhold Chemical Corporation, as a binder. Equivalent amounts of these two binders were used. Primacor has a 20 percent carboxylation while Synthemul 40-504 has to 1 to 3 percent carboxylation. In each case the superabsorbent particles were adhered to the fibers. However, when these treated fibers were passed through a hammer mill, fewer superabsorbent particles separated from the fibers treated with the higher carboxyl group containing binder than separated from the fibers treated with the lower carboxyl group containing binder. Both binders were substantially better at retaining superabsorbent particles than binders which lacked free carboxyl groups. The carboxyl groups are believed to allow for hydrogen bonding between the particles and the binder.

Fibers produced in the manner of these examples were formed into insert pads 14 and combined with dispersion pads 16 to form composite pad structures. These composite pads were then incorporated into disposable diapers.

Having illustrated and described the principles of our invention with reference to several preferred embodiments and examples, it should be apparent to those of ordinary skill in the art that such embodiments of our invention may be modified in detail without departing from such principles. We claim as our invention all such modifications as come within the true spirit and scope of the following claims.

We claim:

1. An absorbent article comprising;
a liquid impermeable backing sheet;
a relatively liquid permeable facing sheet;
a composite absorbent pad positioned between the backing sheet and the facing sheet, the composite pad comprising a liquid dispersion pad and a substantially bonded insert pad, the insert pad being positioned between the facing sheet and overlying the liquid dispersion pad so as to permit flow of liquid to the insert pad without passage through the liquid dispersion pad;
the liquid dispersion pad comprising fibers and assisting in dispersing liquid passing through the facing sheet; and
the insert pad including fibers at least partially coated with a binder material, the fibers being bound together by the binder material to form the substantially bonded insert pad, the fibers also having superabsorbent particles adhered to the fibers by the binder material, the insert pad having a dry weight, the superabsorbent particles being present in a range of from about ten percent to about eighty percent of the dry weight of the insert pad.

2. An absorbent article according to claim 1 in which the insert pad has a density of from about 0.05 grams per cubic centimeter to about 0.30 grams per cubic centimeter.

3. An absorbent article according to claim 2 in which the dispersion pad has a density of from about 0.05 grams per cubic centimeter to about 0.15 grams per cubic centimeter.

4. An absorbent article according to claim 1 in which the insert pad has a density of from about 0.18 grams per cubic centimeter to about 0.22 grams per cubic centimeter.

5. An absorbent article according to claim 4 in which the dispersion pad has a density of from about 0.08 grams per cubic centimeter to about 0.13 grams per cubic centimeter.

6. An absorbent article according to claim 1 in which the liquid dispersion pad and insert pad are wrapped in a nonwoven liquid permeable tissue.

7. An absorbent article according to claim 6 in which the tissue has a basis weight of no greater than about sixty grams per square meter.

8. An absorbent article according to claim 1 in which the insert pad has a taber stiffness of no greater than about five.

9. An absorbent article according to claim 1 in which the insert pad has a taber stiffness of less than seven.

10. An absorbent article according to claim 1 in which the binder material comprises a binder with from about 0.5 to about thirty percent free carboxyl groups.

11. An absorbent article according to claim 1 in which the insert pad has a vertical wicking rate which is no greater than about thirty-five seconds per inch of vertical height of said insert pad.

12. An absorbent article according to claim 1 in which the binder material includes a surfactant material.

13. An absorbent article according to claim 1 for use on a user about said user's front, back and buttocks, the article having a top, front portion positioned against the front of the user when worn and a back portion positioned against the back and buttocks of the user when worn, the liquid dispersion pad having a surface area and being substantially co-extensive in length with the front and back portions of the absorbent article, the insert pad having a surface area which is sized smaller than the surface area of the liquid dispersion pad, the insert pad overlying approximately no more than about twenty to eighty percent of the surface area of the liquid dispersion pad with the insert pad being positioned toward the front portion of the absorbent article.

14. An absorbent article according to claim 13 in which the liquid dispersion pad and the insert pad each have respective side edges, at least one side edge of the insert pad being spaced inwardly from the side edges of the liquid dispersion pad.

15. An absorbent article according to claim 14 in which the liquid dispersion pad has a length and in which at least one side edge of the insert pad is spaced at least about five millimeters from the respective adjacent side edges of the liquid dispersion pad and in which the insert pad extends approximately no more than about three-quarters of the length of the liquid dispersion pad.

16. An absorbent article according to claim 1 in which the insert pad includes hydrophilic fibers which lack the binder material, the other fibers in the insert pad being continuously coated with the binder material.

17. An absorbent article comprising:
a liquid impermeable backing sheet;
a relatively liquid permeable facing sheet;
a composite absorbent pad positioned between the backing sheet and the facing sheet, the composite pad comprising a liquid dispersion pad and a substantially bonded insert pad;
the liquid dispersion pad comprising fibers and assisting in dispersing liquid passing through the facing sheet; and
the insert pad including fibers at least partially coated with a binder material, the fibers being bound together by the binder material to form the substantially bonded insert pad, the fibers also having superabsorbent particles adhered to the fibers by the binder material, the insert pad having a dry weight, the superabsorbent particles being present in a range of from about ten percent to about eighty percent of the dry weight of the insert pad; the insert pad being positioned between the facing sheet and the liquid dispersion pad, the insert pad having a major surface which is not overlaid by the liquid dispersion pad so as to receive liquid passing through the facing sheet and wherein the fibers at least partially coated with the binder material are continuously coated with a thermoplastic binder material and in which the insert pad is thermobonded.

18. An absorbent article according to claim 17 in which the insert pad includes from about five percent to about twenty-five percent hydrophilic fibers by dry weight.

19. A disposable diaper comprising:
 a liquid impermeable backing sheet;
 a relatively liquid permeable facing sheet;
 a liquid dispersion pad comprised of fibers positioned between the backing and facing sheets, the liquid dispersion pad having a density from about 0.05 grams per cubic centimeter to about 0.15 grams per cubic centimeter, the liquid dispersion pad also having a basis weight of from about 150 grams per square meter to about 350 grams per square meter; and
 a densified bonded insert pad positioned between the dispersion pad and facing sheet, the insert pad having a major surface which is not overlaid by the liquid dispersion pad so as to receive liquid passing through the facing sheet, the insert pad comprising fibers at least partially coated with a thermoplastic binder material, the insert pad being heat bonded with the binder material interconnecting the fibers, the fibers also having superabsorbent particles adhered thereto by the binder material, the superabsorbent particles being present in an amount of from approximately ten to eighty percent by dry weight of the insert pad, the insert pad being densified to a density of from about 0.05 grams per cubic centimeter to about 0.3 grams per cubic centimeter, and the insert pad having a basis weight of from about 250 to about 800 grams per square meter.

20. A disposable diaper according to claim 19 in which the insert pad has a taber stiffness of no greater than about five.

21. A disposable diaper according to claim 19 in which the insert pad comprises from about five to about twenty-five percent uncoated hydrophilic fibers together with the at least partially coated fibers.

22. A disposable diaper according to claim 19 in which the at least partially coated fibers are continuously coated with the binder material and the fibers being adhered to the superabsorbent particles by the binder such that the superabsorbent particles are not continuously coated with the binder.

23. A disposable diaper according to claim 19 in which the binder material includes a surfactant material.

24. A disposable diaper according to claim 19 in which the insert pad is positioned against the liquid dispersion pad and is thermobonded to the liquid dispersion pad.

25. A disposable diaper according to claim 24 in which the liquid dispersion pad comprises wood pulp fiber and thermoplastic containing fibers.

26. A disposable diaper according to claim 19 in which the insert pad and the liquid dispersion pad are pressed together to entangle the fibers of said pads.

27. A disposable diaper for use by a user with a front and back comprising:
 a liquid impermeable backing sheet;
 a relatively liquid permeable facing sheet;
 a liquid dispersion pad having an area and a length and being comprised of fibers, the dispersion pad being positioned between the backing and facing sheets, the liquid dispersion pad having a density of from about 0.08 grams per cubic centimeter to about 0.13 grams per cubic centimeter;
 a substantially bonded insert pad positioned between the facing sheet and the liquid dispersion pad, the insert pad including fibers substantially continuously coated with a thermoplastic containing binder material, the fibers being thermobonded together by the binder material to form a substantially bonded insert pad, the fibers also having superabsorbent particles adhered to the fibers by the binder material, the insert pad having a dry weight, the superabsorbent particles being present in a range of from about forty percent to about sixty percent of the dry weight of the insert pad, the insert pad being densified to a density of from about 0.18 grams per cubic centimeter to about 0.22 grams per cubic centimeter;
 the disposable diaper having a top front portion positioned against the from of the user when worn and a back portion positioned against the back of the user when worn, the liquid dispersion pad having a surface area and a length which is substantially co-extensive in length with the front and back portions of the disposable diaper, the insert pad having a surface area sized smaller than the surface area of the liquid dispersion pad, the insert pad overlying approximately twenty to eighty percent of the surface area of the liquid dispersion pad with the insert pad being positioned toward the front portion of the disposable diaper, the liquid dispersion pad and the insert pad each having respective side edges, at least one side edge of the insert pad being spaced inwardly from the side edges of the liquid dispersion pad, and in which the insert pad extends approximately no more than about three-quarters of the length of the liquid dispersion pad.

28. A disposable diaper according to claim 27 in which the binder material includes a surfactant material.

29. A disposable diaper according to claim 27 in which the liquid dispersion pad and insert pad are wrapped in a nonwoven liquid permeable tissue.

30. A disposable diaper according to claim 27 in which the liquid dispersion pad comprises wood pulp fiber and no more than about twenty-five percent by weight thermoplastic containing fibers, the thermoplastic containing fibers assisting in thermobonding the insert pad to the liquid dispersion pad.

31. A disposable diaper according to claim 30 in which the insert pad has a basis weight of from about 250 grams per square meter to about 800 grams per square meter and a taber stiffness of no greater than about five, the liquid dispersion pad having a basis weight of from about 150 grams per square meter to about 350 grams per square meter.

32. A disposable diaper according to claim 31 in which the insert pad has a basis weight of about 500 grams per square meter, a taber stiffness of from two to four, and the liquid dispersion pad has a basis weight of about 250 grams per square meter.

33. An absorbent article comprising:
 a composite absorbent pad structure, the composite pad structure comprising an insert pad and a liquid dispersion pad, said insert pad and liquid dispersion pad having surfaces that interface, said insert pad including fibers at least partially coated with a binder material, the fibers being bound together by the binder material to form a substantially bonded insert pad, the fibers also having superabsorbent particles adhered to the fibers by the binder material, the insert pad having a dry weight, the superabsorbent particle being present in a range of from about ten percent to about eighty percent of the dry weight of the insert pad, the insert pad having a taber stiffness of from about two to about five, and said liquid dispersion pad comprised of fibers for assisting in dispersing liquid throughout the insert pad and in which the insert pad has a vertical wicking rate of no more than about twenty-three seconds per inch of vertical height.

* * * * *